US010455887B2

(12) United States Patent
London

(10) Patent No.: US 10,455,887 B2
(45) Date of Patent: Oct. 29, 2019

(54) FITNESS APPARATUS

(71) Applicant: Justin London, Chicago, IL (US)

(72) Inventor: Justin London, Chicago, IL (US)

( * ) Notice: Subject to any disclaimer, the term of this patent is extended or adjusted under 35 U.S.C. 154(b) by 35 days.

(21) Appl. No.: 15/160,700

(22) Filed: May 20, 2016

(65) Prior Publication Data

US 2016/0338441 A1 Nov. 24, 2016

Related U.S. Application Data

(60) Provisional application No. 62/164,562, filed on May 21, 2015.

(51) Int. Cl.
*A43B 23/00* (2006.01)
*A43B 3/00* (2006.01)
(Continued)

(52) U.S. Cl.
CPC ............... *A43B 3/001* (2013.01); *A43B 5/00* (2013.01); *G01S 19/19* (2013.01); *H05B 37/0209* (2013.01); *A41D 1/002* (2013.01); *A43B 1/0036* (2013.01); *A43B 1/0072* (2013.01); *A43B 3/0005* (2013.01); *A43B 3/0078* (2013.01); *A43B 13/14* (2013.01); *A43B 13/20* (2013.01); *A61B 5/11* (2013.01); *A61B 5/4866* (2013.01); *A61B 5/6807* (2013.01); *A61B 2562/0219* (2013.01);
(Continued)

(58) Field of Classification Search
CPC ...... H05B 37/029; G01S 19/19; A43B 1/0036
USPC .................................................. 2/69; 36/137
See application file for complete search history.

(56) References Cited

U.S. PATENT DOCUMENTS 5,052,131 A * 10/1991 Rondini ............... A43B 1/0072
36/11.5
5,452,269 A * 9/1995 Cherdak ................ G04B 47/00
36/132
(Continued)

FOREIGN PATENT DOCUMENTS

CN 204120323 U 1/2015
CN 204120325 U 1/2015
(Continued)

OTHER PUBLICATIONS

Wenling Rechargeable USB Led Micro Led String Shoes Lights; printed Apr. 27, 2015 from website www.alibaba.com/product-detail/wenling-rechargeable-USB-led-micro-led_60081394111.html?s=p; 10 pages.

*Primary Examiner* — Timothy K Trieu
(74) *Attorney, Agent, or Firm* — Dinsmore & Shohl LLP

(57) ABSTRACT

A fitness apparatus for a shoe is disclosed. The shoe includes a top portion, a sole portion, and an interior portion. Additionally, the shoe includes one or more processors, one or more memory modules, and a plurality of lighting elements. The shoe further includes a power supply, a lighting power switch, a satellite antenna, and machine readable instructions stored in the one or more memory modules that cause the shoe to perform at least one of determining a distance travelled between a start position and an end position, determining calories burned during the distance travelled, activating the plurality of lighting elements in a lighting mode in response to a signal received from the lighting power switch, and sending fitness data indicative of the distance travelled, calories burned, or the lighting mode, when executed by the one or more processors.

17 Claims, 11 Drawing Sheets

(51) Int. Cl.
  *A43B 5/00*    (2006.01)
  *G01S 19/19*   (2010.01)
  *H05B 37/02*   (2006.01)
  *A43B 13/14*   (2006.01)
  *A41D 1/00*    (2018.01)
  *A43B 1/00*    (2006.01)
  *A61B 5/11*    (2006.01)
  *A61B 5/00*    (2006.01)
  *A43B 13/20*   (2006.01)

(52) U.S. Cl.
  CPC ....... *A63B 2220/20* (2013.01); *A63B 2220/30* (2013.01); *H05B 37/0272* (2013.01)

(56) References Cited

U.S. PATENT DOCUMENTS

| | | | | |
|---|---|---|---|---|
| 5,457,900 | A * | 10/1995 | Roy | G09G 3/005 |
| | | | | 315/323 |
| 5,471,405 | A * | 11/1995 | Marsh | A43B 3/0005 |
| | | | | 36/114 |
| 5,599,088 | A * | 2/1997 | Chien | A43B 1/0072 |
| | | | | 200/61.45 R |
| 6,434,485 | B1 * | 8/2002 | Beason | G01C 5/06 |
| | | | | 342/120 |
| 7,200,517 | B2 * | 4/2007 | Darley | A43B 3/0005 |
| | | | | 702/160 |
| 8,641,220 | B1 | 2/2014 | Lin | |
| 2007/0011919 | A1 * | 1/2007 | Case, Jr. | A43B 1/0036 |
| | | | | 36/132 |
| 2009/0288317 | A1 * | 11/2009 | Forbes | A43B 3/00 |
| | | | | 36/136 |
| 2011/0308113 | A1 * | 12/2011 | Hartford | A43B 1/0027 |
| | | | | 36/136 |
| 2014/0157632 | A1 | 6/2014 | Kim | |
| 2015/0181314 | A1 * | 6/2015 | Swanson | H04Q 9/00 |
| | | | | 340/870.07 |
| 2015/0237949 | A1 * | 8/2015 | Poulos | A43B 3/001 |
| | | | | 340/435 |

FOREIGN PATENT DOCUMENTS

| | | |
|---|---|---|
| CN | 204191690 U | 3/2015 |
| JP | 3196251 U | 2/2015 |

* cited by examiner

FITNESS APPARATUS

CLAIM OF PRIORITY

This application claims the benefit of U.S. Provisional Application No. 62/164,562, entitled "Luminous Shoes, Apparel, and Gear with Tracking Locator Capabilities," filed May 21, 2015, the entirety of which is hereby incorporated by reference.

TECHNICAL FIELD

Embodiments described herein generally relate to fitness apparatuses, and more specifically, to fitness apparatuses having a plurality of lighting elements used in conjunction with shoes or clothing items to track a distance travelled, measure calories burned and indicate a location of the fitness apparatus.

BACKGROUND

Shoes and apparel that have luminous lights disposed in them are largely used by children and adults. These shoes and apparel may be used for safety reasons, for example, while running outside at night. These shoes and apparel might also have a decorative aspect to them. In shoes and apparel that are currently available, however, consumers are unable to control the color of the lights, and the frequency with which the lights flash. Further, these shoes which have lights that blink when a person walks, jumps or runs can easily drain the battery placed within the shoes. These batteries are non-rechargeable, and at times, hard to replace. Further, shoes or apparel that are able to track fitness details during a workout, such as the distance traveled during a run, or the calories burned during the run cannot be measured by the shoes/apparel itself. While there may be other fitness devices that are capable of performing such functionalities, these fitness devices need to be separately worn.

Accordingly, a need exists for alternative fitness apparatuses that are able to activate desired colors and lighting patterns displayed on the shoe and apparel, and at the same time track various fitness details.

SUMMARY

According to one embodiment, a fitness apparatus for a shoe is disclosed. The shoe includes a top portion, a sole portion below the top portion, and an interior portion an inside of the top portion. Additionally, the shoe includes one or more processors, one or more memory modules communicatively coupled to the one or more processors, and a plurality of lighting elements coupled to the one or more processors. The shoe further includes a power supply, providing power to the plurality of lighting elements, a lighting power switch configured to control the plurality of light elements disposed on the shoe, and a network interface hardware for sending and receiving fitness data. The shoe further includes machine readable instructions stored in the one or more memory modules that cause the shoe to perform at least one of determining a distance travelled between a start position and an end position, determining calories burned during the distance travelled, activating the plurality of lighting elements in a lighting mode in response to a signal from the lighting power switch, and sending fitness data indicative of the distance travelled, calories burned, or the lighting mode, when executed by the one or more processors.

In another embodiment, a fitness apparatus for a shoe is disclosed. The shoe includes a top portion, a sole portion below the top portion, and an interior portion an inside of the top portion. Additionally, the shoe includes one or more processors, one or more memory modules communicatively coupled to the one or more processors, and a plurality of lighting elements coupled to the one or more processors. The shoe further includes a power supply, providing power to the plurality of lighting elements, a lighting power switch configured to control the plurality of light elements disposed on the shoe, and a network interface hardware for sending and receiving fitness data. The shoe further includes machine readable instructions stored in the one or more memory modules that cause the shoe to perform at least one of determining a current position, determine whether the current position is within a pre-determined radius from a reference position, activating the plurality of lighting elements in a lighting mode, and sending fitness data indicative of the current position or the lighting mode, when executed by the one or more processors.

In yet another embodiment, a fitness apparatus for a clothing item is disclosed. The clothing item includes an exterior portion, an interior portion lining an inside of the exterior portion. Additionally, the clothing item includes one or more processors, one or more memory modules communicatively coupled to the one or more processors, and a plurality of lighting elements coupled to the one or more processors. The clothing item further includes a power supply providing power to the plurality of lighting elements, a lighting power switch configured to control the plurality of lighting elements, and a network interface hardware for sending and receiving fitness data. The clothing item further includes machine readable instructions stored in the one or more memory modules that cause the clothing item to perform at least one of determining a distance travelled between a start position and an end position, determining calories burned during the distance travelled, determine a current position, activating the plurality of lighting elements in a lighting mode in response to a signal from the lighting power switch, and sending fitness data indicative of the distance travelled, the calories burned, the current position, or the lighting mode, when executed by the one or more processors.

Additional features and advantages of the fitness apparatus described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
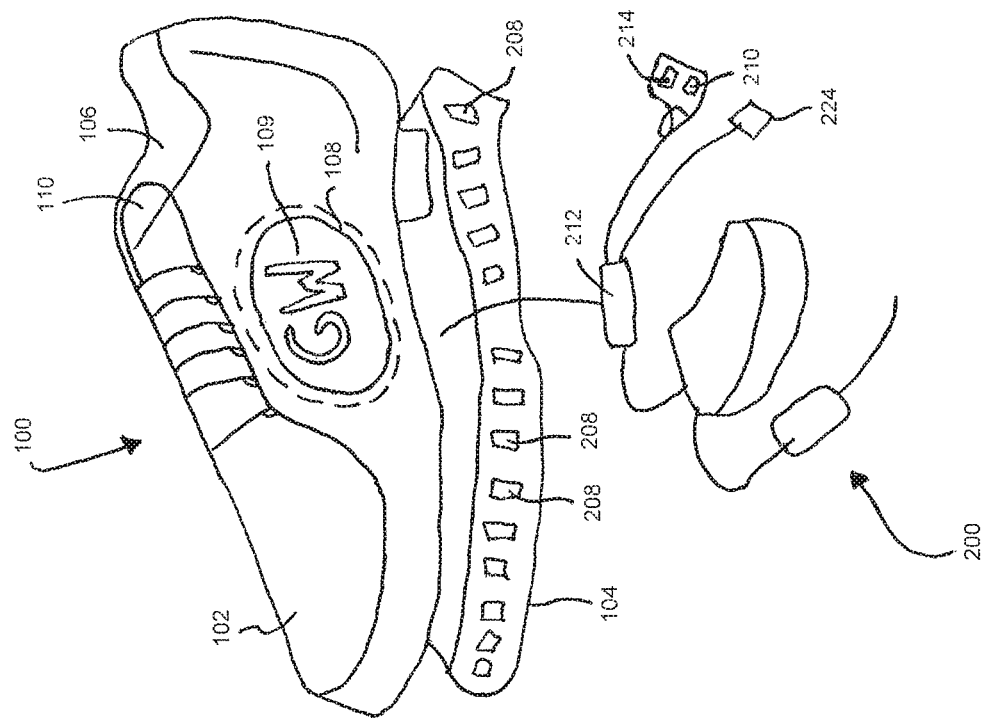
FIG. 1 illustrates a fitness apparatus and a shoe, according to one or more embodiments shown and described herein.

Reference will now be made in detail to embodiments of the fitness apparatus described herein, examples of which are illustrated in the accompanying drawings. Whenever possible, the same reference numerals will be used throughout the drawings to refer to the same or like parts. Referring to the figures generally, embodiments of the fitness apparatus provided herein include the fitness apparatus coupled to shoes or apparel. The fitness apparatus determines a distance traveled between a start position and an end position, a current position, and calculates a distance travelled, and determine calories burned while traversing from the start position to the end position. Further, fitness apparatus determines the current position of the fitness apparatus. This information is sent to a display device. Additionally, the fitness apparatus includes a plurality of lighting elements coupled to the shoe. The plurality of lighting elements is configured to operate in various lighting modes and emit different colors.

Embodiments of the fitness apparatus are described herein specifically with respect to shoes, or apparel. However, the fitness apparatus may be used with other daily use items such as handbags, backpacks, keys or key chains, eye wear, and the like. In addition to the various fitness tracking capabilities of the fitness apparatus, it may also be used without such capabilities for solely aesthetic or fashionable reasons.

Referring to FIG. 1, an example embodiment of the fitness apparatus 200 coupled to a shoe 100 is shown. The shoe includes a top portion 102, a sole portion 104, an interior portion 106, a tongue portion 110, and a logo portion 108. While the shoe 100 shown in FIG. 1 is a sneaker, the shoe 100 may be a heeled shoe, a platform shoe, a sandal, a boot, a flip flop or the like. Additionally, the shoe 100 may be a women's shoe, a men's shoe or a child's shoe. The top portion 102 of the shoe 100 is configured to accommodate a human foot. Further, the shoe 100 includes the sole portion 104 placed beneath the top portion 102. In embodiments, the sole portion 104 is attached to the top portion 102 by using an adhesive, stitching the two portions together, or the like. In embodiments, the sole portion 104 may be made of plastic, resin, foam, hybrid foam, or gel. In some embodiments, the sole portion 104 may be transparent or translucent. In embodiments, the sole portion 104 may have recesses surrounding the edges of the sole portion 104. The interior portion 106 of the shoe 100 lines the top portion 102 and is in direct contact with the human feet, once placed into the shoe 100. The at least one logo portion accommodates a logo 109 on an exterior portion of the top portion 102 of the shoe. In some embodiments, more than one logo 109 may be placed on an exterior portion and interior portion 106 of the shoe 100.

Still referring to FIG. 1, the fitness apparatus 200 is also shown. In this embodiment, the fitness apparatus 200 includes the plurality of lighting elements 208 disposed at the sole portion 104 of the shoe 100. Also shown is the circuitry of the fitness apparatus 200 which includes a lighting power switch 210, a GPS power switch 214, a charging port 224 and a power supply 212. The fitness apparatus 200 is communicatively coupled to a network 222 by the network interface hardware 218. The fitness apparatus 200 will be described in further detail with respect to FIG. 2.

Figure 2:
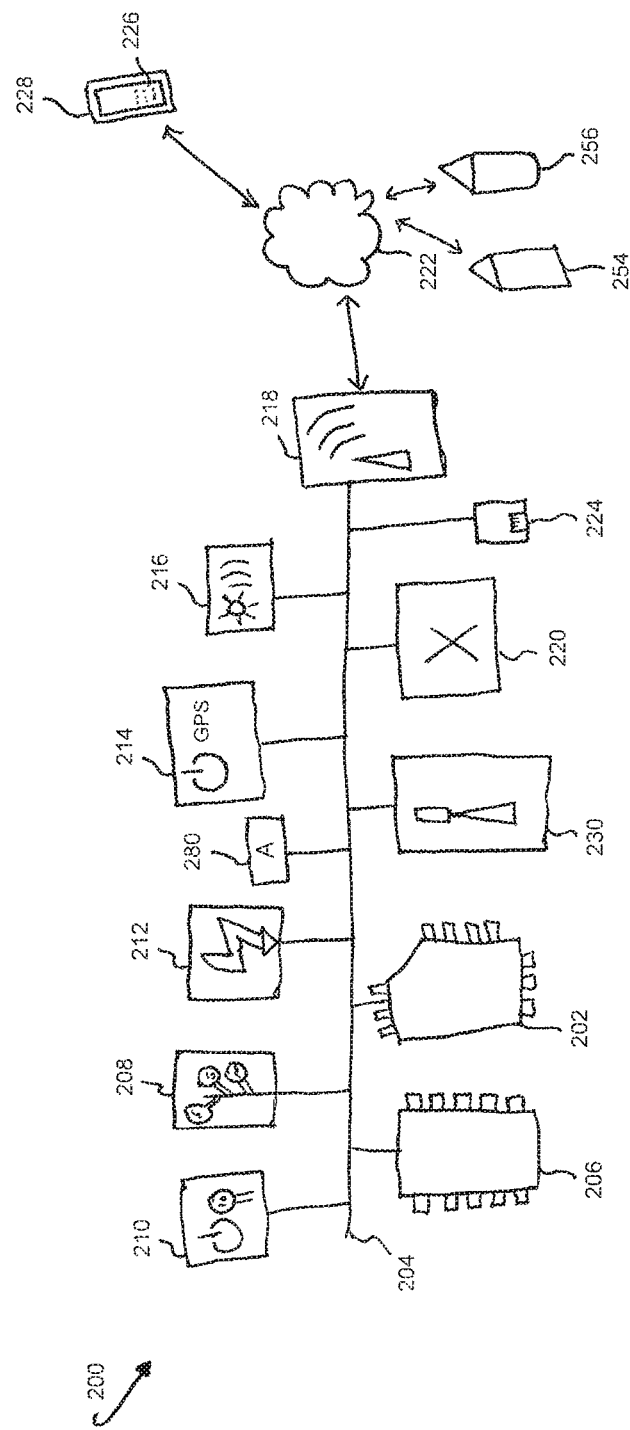
FIG. 2 illustrates the various components of the fitness apparatus, according to one or more embodiments shown and described herein.

Referring now to FIG. 2, the fitness apparatus 200 includes one or more processors 202, one or more memory modules 206, a communication path 204, the plurality of lighting elements 208, the lighting power switch 210, the power supply 212, the GPS power switch 214, a light sensor 216, a network interface hardware 218, the charging port 224, a transducer 220, a display device 228, and a satellite antenna 230.

Still referring to FIG. 2, the fitness apparatus 200 includes the communication path 204. The communication path 204 may be formed from any medium that is capable of transmitting a signal such as, for example, conductive wires, conductive traces, optical waveguides, or the like. Moreover, the communication path 204 may be formed from a combination of mediums capable of transmitting signals. In one embodiment, the communication path 204 comprises a combination of conductive traces, conductive wires, connectors, and buses that cooperate to permit the transmission of electrical data signals to components such as processors, memories, sensors, input devices, output devices, and communication devices. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium. The communication path 204 communicatively couples the various components of the fitness apparatus 200. As used herein, the term "communicatively coupled" means that coupled components are capable of exchanging data signals with one another such as, for example, electrical signals via conductive medium, electromagnetic signals via air, optical signals via optical waveguides, and the like.

As noted above, the fitness apparatus 200 includes the one or more processors 202. Each of the one or more processors 202 may be any device capable of executing machine readable instructions. Accordingly, each of the one or more processors 202 may be a controller, an integrated circuit, a microchip, a computer, or any other computing device. The one or more processors 202 are communicatively coupled to the other components of the fitness apparatus 200 by the communication path 204. Accordingly, the communication path 204 may communicatively couple any number of processors with one another, and allow the modules coupled to the communication path 204 to operate in a distributed computing environment. Specifically, each of the modules may operate as a node that may send and/or receive data.

As noted above, the fitness apparatus 200 includes the one or more memory modules 206. Each of the one or more memory modules 206 of the fitness apparatus 200 is coupled to the communication path 204 and communicatively coupled to the one or more processors 202. The one or more memory modules 206 may comprise RAM, ROM, flash memories, hard drives, or any device capable of storing machine readable instructions such that the machine readable instructions can be accessed and executed by the one or more processors 202. The machine readable instructions may comprise logic or algorithm(s) written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled into machine readable instructions and stored on the one or more memory modules 206. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. The one or more memory modules 206 may include program embedded software that enables a user to select or enter the type of fitness tracking desired, and sync it to the display device 228. The "syncing" ensures that the display device 228 and fitness apparatus 200 can communicate with one another through one of RFID data transmission, GPS data transmission, or a combination thereof such that the fitness apparatus 200 is able to perform various fitness determination tasks.

In some embodiments, the one or more memory modules 206 includes one or more RFID decoder algorithms, such as an automatic RFID code recognition engine that processes RFID input signals received from the RFID scanner and/or extracts information from such signals, as will be described in further detail below. Furthermore, the one or more memory modules 206 include machine readable instructions that, when executed by the one or more processors 202, cause the fitness apparatus 200 to perform the actions described below.

Referring to FIG. 2, the fitness apparatus 200 includes the plurality of lighting elements 208. The plurality of lighting elements 208 are coupled to the one or more processors 202. The plurality of lighting elements 208 may be disposed at the shoe 100, or apparel, such as a track warm-up suit jacket (shown in FIG. 9) or a handbag or backpack (as shown in FIGS. 10A and 10B). In embodiments where the fitness apparatus 200 is used with the shoe 100, the plurality of lighting elements 208 may be placed in the sole portion 104 of the shoe 100. Further, in some embodiments, the sole portion 104 of the shoe 100 may be transparent or translucent such that the plurality of lighting elements 208 are visible through the sole portion 104 of the shoe 100. In some embodiments, the plurality of lighting elements 208 may be disposed around the logo portion 108 of the shoe 100. In some embodiments, the logo portion 108 itself may be made of the plurality of lighting elements 208. In embodiments, the logo 109 may be made of the plurality of lighting elements 208 and may be detachable. In embodiments, the plurality of lighting elements 208 may be LED lights, electroluminescence (EL) lights, incandescent lights, HID lights, fluorescent lights, halogen lights or the like. In some embodiments, the plurality of lighting elements 208 can display between about 20 to about 30 different colors.

Still referring to FIG. 2, machine readable instructions stored in the one or more memory modules 206 cause the fitness apparatus 200 to activate the plurality of lighting elements 208 in a lighting mode when executed by the one or more processors 202. The lighting mode of the plurality of lighting elements 208 is the frequency with which the plurality of lighting elements 208 emit light. As used herein, the lighting mode refers to a pre-determined pattern and/or color emitted by the plurality of lighting elements 208. In embodiments, various lighting modes by be stored in the one or more memory modules 206, and executed by the one or more processors 202. Examples of lighting modes include, but are not limited to strobe lighting, blinking lighting, static lighting, fading lighting or a combination thereof. In some embodiments, other types of lighting modes may be designed or programmed by the user such as a mode to sync the lighting elements to music or rhythms (or to change the static color as various running distances are reached.) In such an embodiment, the shoe 100 could include a built-in speaker in the heel of the shoe 100, for instance, and process/amplify music and sound externally through stored in the one or more memory modules 206 and execute by one or more processors 202 to the plurality of lighting elements 208 by wires. The colors in the plurality of lighting elements 208 could change to the beat of the sound.

The shoe 100 may include shoe laces fitted with the plurality of lighting elements 208, such as LEDs. Such laces may have a lithium ion battery in a plastic casing contained a PCB with an on/off switch on the outside connected to the left and right part of the lace. The shoe laces get laced through the eyelids along the tongue portion 110. The LEDs are connected by wire to the battery inside the casing and illuminate when the switch is turned on. Thus, the laces can be illuminated separately from the LED soles.

In some embodiments, machine readable instructions stored in the one or more memory modules 206 cause the fitness apparatus 200 to activate the plurality of lighting elements 208 to display a pre-selected lighting mode in response to obtaining a pre-selected distance goal when executed by the one or more processors 202. The pre-selected distance goal is the distance input by a user that is indicative of a distance that the user wants to achieve by performing activities like walking, jogging, running. In embodiments, machine readable instructions stored in the one or more memory modules 206 cause the fitness apparatus 200 to activate the plurality of lighting elements 208 to display a pre-selected lighting mode in response to obtaining a pre-selected calories goal when executed by the one or more processors 202. The pre-selected calories goal is the amount of calories input by a user that is indicative of an amount of calories the user wants to burn by performing various physical activities. In such embodiments, the pre-selected distance goal and the pre-selected calories goal may be entered by the user using a tactile input hardware 226. In embodiments, the tactile input hardware 226 may be a part of the display device 228 as shown in FIG. 2, or may be a separate component. In some embodiments, a user is also able to input the pre-selected lighting mode using the tactile input hardware 226.

Referring to FIG. 2, the machine readable instructions stored in the one or more memory modules 206 cause the fitness apparatus 200 to activate the plurality of lighting elements 208 to display a first pre-selected lighting mode in response to charging the shoe 100, and activate the plurality of lighting elements to display a second pre-selected lighting mode in response to completion of the charging when executed by the one or more processors 202. In embodiments, as the shoe 100 or apparel such as a jacket (shown in FIG. 9) or gear, such as a handbag or backpack (as shown in FIGS. 10A and 10B), is being charged using the charging port 224, different pre-selected lighting modes may be displayed on the fitness apparatus 200. For example, while the shoe 100 is charging, a red blinking light may be displayed on the plurality of lighting elements 208. After the shoe 100 has been fully charged, a green solid light may be displayed on the plurality of lighting elements 208. In embodiments, the plurality of lighting elements 208 may be blinking during charging, and will become static (non-blinking) when fully charged. The first and second pre-selected lighting modes may be input by the tactile input hardware 226.

As shown in FIG. 2, the fitness apparatus 200 also includes the lighting power switch 210. The lighting power switch 210 is configured to control the plurality of lighting elements 208. That is, the lighting power switch 210 is configured to turn on or turn off the plurality of lighting elements 208. In some embodiments, the lighting power switch 210 may be a button that can be clicked using the user's hands. In other embodiments, tapping the shoe 100 may be sufficient to operate the lighting power switch 210. In embodiments, the lighting power switch 210 is disposed on the shoe 100. In embodiments where the fitness apparatus 200 is used with apparel, such as a jacket, or gear, such as a handbag, the lighting power switch 210 may be disposed within the interior portion of the jacket or handbag. Further, in some embodiments, a lighting power switch 210 may not be provided, and the plurality of lighting elements 208 may be turned on, turned off, dimmed or controlled in other ways from the tactile input 226 on the display device 228 via an app or program.

In embodiments, the lighting power switch 210 may also be configured to control the intensity of the plurality of lighting elements 208. In some embodiments, the lighting power switch 210 may have an on mode, an off mode, and an intermediate mode which dims the light emitted by the plurality of lighting elements 208. In some embodiments, the lighting power switch 210 may be configured to have more than one intermediate mode which allows the user to adjust the brightness or dimness emitted by the plurality of lighting elements 208. In some embodiments, a dimness switch separate from the lighting power switch 210 may be disposed at the shoe 100 to control the brightness/dimness emitted by the plurality of lighting elements 208.

In some embodiments, the lighting power switch 210 may also be used to rotate or change the colors emitted by the plurality of lighting elements 208. In these embodiments, clicking the lighting power switch 210 allows a user to select a color to be emitted by the plurality of lighting elements 208. In some embodiments, a user can select different lighting modes emitted by the plurality of lighting elements 208 by using the lighting power switch 210. In embodiments, a speed for lighting modes can also be controlled by the lighting power switch 210. For example, by holding the lighting power switch 210 down for a few seconds, the plurality of lighting elements 208 may emit different lighting modes. A user is then allowed to select which lighting mode she would like the plurality of lighting elements 208 to emit. In other embodiments, the lighting power switch 210 and lighting modes may be controlled remotely via an app on a hand-held device using wireless communication signals between a transmitter in the display device 228 and the satellite antenna 230 in shoe 100. Additionally, in embodiments, the lighting power switch 210 may also be configured to change RBG patterns emitted by the plurality of lighting elements 208 to change the color emitted.

Referring to FIG. 2, the fitness apparatus 200 includes the power supply 212. The power supply 212 is configured to provide power to the plurality of lighting elements 208 and other components of the fitness apparatus 200. The power supply 212 may be a battery. In some embodiments, the power supply 212 may be a rechargeable battery. In some embodiments, the battery is a lithium battery that supplies power to the different components of the fitness apparatus 200. In some embodiments, the power supply includes embedded chips. The embedded chips may include a Radio Frequency Identification (RFID) chip, a Global Position System (GPS) chip, a Bluetooth® chip, WiFi chip, or a combination thereof, supporting wireless and GSM network data communications such as general packet radio system (GPRS).

By way of example, the GPS chip could utilize a SIM968 module which is a compact Quad-Bank GSM/GPRS-enable module base on a PNX4851 platform also equipped with GNSS technology for satellite navigation. The complete design in a SMT type chip makes it easy to integrate GSM/GPRS&GPS as an all-in-one-solution. It is programmed by a SIM application toolkit and utilizes a supply voltage range: V-BAT: 3.2V to 4.8V, V-GPS: 2.8V to 4.3V, VCHG: 5V.

In some embodiments, the fitness apparatus 200 includes a GPS chip which may be a part of the power supply 212 or a separate component. Other embodiments may not include a separate GPS chip such as embodiments that include the satellite antenna 120 and include readable instructions in the one or more memory modules 206 that perform the GPS-related functions described herein when executed by the one or more processors 202. In embodiments, the GPS chip is coupled to the one or more memory modules 206 and the one or processors 202. In embodiments, the fitness apparatus 200 is configured to obtain and update positional information of the user. The GPS chip may be able to obtain and update positional information based on geographical coordinates, i.e. latitudes and longitudes, or via electronic positional information received through satellites. In embodiments, machine readable instructions stored in the one or more memory modules 206 cause the fitness apparatus 200 to perform various fitness determination tasks when executed by the one or more processors 202.

In embodiments, the various fitness determination tasks include determining a start position and an end position, and determining a distance traveled between the start portion and the end position. The start position may be a position at which the user begins to use the fitness apparatus 200. In embodiments, a user may be allowed to set and/or re-set the start position using the GPS power switch 214 or the tactile input hardware 226. The end position may be a position at which a user has completed her use of the fitness apparatus. For example, the start position may be the geographical coordinates at which the user begins her workout and the end position may be the geographical coordinates at which the user ends her workout. In embodiments, the distance traveled between the start position and the end position is determined. The distance traveled may be measured in kilometers or miles, as per the user's preference. Another fitness determination task may include determining a route traveled between the start position and the stop position. In embodiments, the route traveled between the start and stop position may be displayed in the form of a map on the display device 228. Further, the start position and the stop position may also be displayed on a map on the display device 228. In embodiments, the fitness apparatus 200 (e.g. using the GPS chip) is configured to track movement information indicating how a user arrived at the end position from the start position. For example, the fitness apparatus 200 (e.g. using the GPS chip) is configured to track when a user makes a left turn, or a right turn, or turns round about, or the like. Such information is tracked while determining the route traveled by the user. In embodiments, the fitness data determined above may be stored in the one or more memory modules 206 and displayed on the display device 228.

In embodiments, the various fitness determination tasks also include determining a current position of the fitness apparatus 200. The current position may be the geographical coordinates at which the fitness apparatus 200 is located at a given time. Further, in embodiments, fitness determination tasks also include determining whether the current position is within a pre-determined radius from a reference position. When the fitness apparatus 200 is outside of the pre-determined radius from the reference position, the fitness apparatus 200 is configured to send, automatically the current position of the fitness apparatus. Further, the fitness apparatus 200 is also configured to send a notification to the display device 228 indicating that the fitness apparatus 200 is no longer within the pre-determined radius. In embodiments, the fitness apparatus 200 may be configured to set up a geofence boundary. This feature may be used for a parent to track the location of her child, and whether the child is within a pre-determined radius of a house, school, day care, and the like. Further, the fitness apparatus 200 may also be configured to map the reference position and the current position on apps such as Google Maps or Google Earth.

In embodiments, fitness data related to the start position, the end position, the distance traveled between the start position and the end position, the current position, the reference position, and the route traveled is received by fitness apparatus 200 (e.g. using the GPS chip) using the satellite antenna 230. As noted above, the fitness apparatus 200 includes the satellite antenna 230 coupled to the communication path 204 such that the communication path 204 communicatively couples the satellite antenna 230 to other modules of the fitness apparatus 200. In embodiments, the satellite antenna 230 is communicatively coupled to the power supply 212 including the GPS chip. The satellite antenna 230 is configured to receive signals from GPS satellites. Specifically, in one embodiment, the satellite antenna 230 includes one or more conductive elements that interact with electromagnetic signals transmitted by GPS satellites. The received signal is transformed into a data signal indicative of the location (e.g., latitude and longitude) of for example, the start position or the end position, or the current position by the one or more processors 202. Additionally, it is noted that the satellite antenna 230 may include at least one of the one or more processors 202 and the one or memory modules 206. The data may then be stored on one of one or more memory modules 206 of the fitness apparatus 200.

Still referring to FIG. 2, in embodiments, the GPS chip in conjunction with a transducer 220 may be configured to determine various fitness determination tasks. In embodiments, fitness determination tasks such as the distance traveled and calories burned during the distance traveled may be calculated based on a kinetic energy movement of the shoe 100. In embodiments, the transducer 220 may be used to calculate the number of times the shoe 100 strikes the ground. For example, the distance traveled may be calculated based on a number of times the shoe 100 strikes the ground while the user is walking, or jogging or running, and a time that it took to traverse the distance traveled. The amount of calories burned may also be computed in a similar way. In embodiments, the transducer 220 may be an active transducer, a passive transducer, a sensor, or an electric actuator.

Referring to FIG. 2, in some embodiments that include a GPS chip, an RFID chip, a Bluetooth chip and a Wifi chip, the GPS chip may be communicatively coupled to the RFID chip, the Bluetooth® chip, and the WiFi chip. The fitness data such as information regarding the start position, the end position, the current position may be sent to the display device 228 via the RFID chip, the Bluetooth® chip, or the WiFi chip. In embodiments, the fitness data may be sent periodically to the display device 228. In one embodiment, the fitness data may be sent to the display device 228 when requested. As a non-limiting example, the current position of the user wearing the fitness apparatus 200 may be sent to the display device 228 when requested or at pre-set time intervals.

Referring to FIG. 2, the fitness apparatus 200 also includes a GPS power switch 214. The GPS power switch 214 is communicatively coupled to the communication path 204. In embodiments, the GPS power switch 214 is communicatively coupled to the GPS chip of the power supply 212. In embodiments, the GPS power switch 214 is configured to turn on or off the GPS capabilities of the fitness apparatus 200. For example, when the GPS power switch 214 is turned off, the GPS chip will not be operational, and therefore, fitness data such as the start position, the end position, the distance traveled, and the like may not be determined by the fitness apparatus 200. In embodiments, to determine such fitness data, the GPS power switch 214 will need to be turned on. In some embodiments, the GPS power switch 214 is configured to control the GPS chip independent of the lighting power switch 210. In some embodiments, the GPS power switch 214 may have power-saving consumption capabilities to maximize GPS signal availability.

As noted above, the fitness apparatus 200 includes the network interface hardware 218 for communicatively coupling the fitness apparatus 200 and a network 222. The network interface hardware 218 is coupled to the communication path 204 such that the communication path 204 communicatively couples the network interface hardware 218 to other modules of the fitness apparatus 200. The network interface hardware 218 can be any device capable of transmitting and/or receiving data via a wireless or cellular network. Accordingly, the network interface hardware 218 can include a communication transceiver for sending and/or receiving data according to any wireless communication standard. For example, the network interface hardware 218 may include a chipset (e.g., antenna, processors, machine readable instructions, etc.) to communicate over wireless computer networks such as, for example, wireless fidelity (WiFi), WiMax, Bluetooth, IrDA, Wireless USB, Z-Wave, ZigBee, or the like. In some embodiments, the network interface hardware 218 includes a Bluetooth transceiver that enables the fitness apparatus 200 to exchange information with the display device 228 via Bluetooth communication.

Still referring to FIG. 2, data from the display device 228 may be provided to the fitness apparatus 200 via the network interface hardware 218. Specifically, the fitness apparatus 200 may include an antenna for communicating over one or more of the wireless computer networks described above. Moreover, the fitness apparatus 200 may include a mobile antenna for communicating with the network 222. Accordingly, the antenna may be configured to send and receive data according to a mobile telecommunication standard of any generation (e.g., 1G, 2G, 3G, 4G, 5G, etc.).

In embodiments, the display device 228 is a portable display device. In some embodiments, the display device 228 may also have one or more memory modules, and one or more processors. Further, the display device 228 may also have a tactile input hardware 226 integrated with the display device 228. In some embodiments, the display device 228 may be a touchscreen. In some embodiments, a user may use to the display device 228 to input the lighting mode, or a pre-selected distance goal or a pre-selected calories goal. In embodiments, the display device 228 is also used to receive fitness data sent through the network interface hardware 218 and display the information received. Fitness data includes information indicative of the distance traveled, the calories burned, the current position or the lighting mode. In embodiments, the display device 228 may be a cell phone, a computer monitor, a laptop, a tablet, a smart watch, or the like.

In embodiments, more than one display device 228 may be communicatively coupled with the fitness apparatus 200. In this instance, fitness apparatus 200 may be configured to send fitness data to some or all of the display devices 228. For example, the fitness apparatus 200 when worn by a child user, may be configured to send fitness data related to the current position of the child wearing the fitness apparatus 200 coupled to the child's display device 228 and a parent user's display device 228. In these embodiments, the tactile input hardware 226 of both the child's display device 228 and the parent's display device 228 may be communicatively coupled to the fitness apparatus 200 such that the tactile input hardware 226 of both devices may be configured to request for fitness data.

Referring to FIG. 2, the network 222 generally includes one or more computing devices configured to receive and transmit data according to a network communication protocol. In some embodiments, the network 222 includes a wired systems such as public switched telephone network (PSTN) or a backhaul networks. In some embodiments, the network 222 includes one or more of a wide area network, a metropolitan area network, the Internet, a satellite network, or the like. Further example networks include but are not limited to GSM, GPRS, and WCDMA. Thus, the network 222 generally include one or more antennas, transceivers, and processors that execute machine readable instructions to exchange data over various wired and/or wireless networks.

In some embodiments, the network 222 can be utilized as a wireless access point by the fitness apparatus 200 to access one or more servers (e.g., a first server 254 and/or a second server 256). The first server 254 and second server 256 generally include processors, memory, and chipset for delivering resources via the network 222. Resources can include providing, for example, processing, storage, software, and information from the first server 254 and/or the second server 256 to the fitness apparatus 200 via the network 222. Additionally, it is noted that the first server 254 or the second server 256 can share resources with one another over the network 222 such as, for example, via the wired portion of the network, the wireless portion of the network, or combinations thereof.

Still referring to FIG. 2, the one or more servers accessible by the fitness apparatus 200 via the network 222 may include third party servers that provide additional capability for performing the functionality described herein. For example, the first server 254 and/or the second server 256 may store the location coordinates (on a GPS map) related to the start position, the end position, the distance traveled, and the route traveled in a database for retrieval by the fitness apparatus 200. It should be understood that the fitness apparatus 200 and/or the display device 228 may be communicatively coupled to any number of servers by way of the network 222.

Still referring to FIG. 2, the fitness apparatus 200 also includes a light sensor 216. In embodiments, the light sensor 216 is communicatively coupled to the one or more processors 202. The light sensor 216 may be an analog light sensor. In some embodiments, non-limiting examples of light sensor 216 include photocells, light-dependent resistors, or photoresistors. The machine readable instructions stored in the one or more memory modules 206 cause the fitness apparatus 200 to activate the plurality of lighting elements 208 to automatically turn on in response to a dark external environment based on a determination by the light sensor 216 when executed by the one or more processors 202. In embodiments, the light sensor 216 is disposed on the exterior portion of the shoe 100. The light sensor 216 detects the amount of light present in an external environment. When light is insufficiently present, the fitness apparatus 200 is configured to automatically turn on the plurality of lighting elements 208. For example, when a user is running outside and the light sensor 216 detects a change in the amount of light in the external environment, i.e. the environment surrounding and outside of the shoe 100, the one or more processors 202 is configured to automatically turn on the plurality of lighting elements 208. Similarly, when the light sensor 216 determines the presence of light in the external environment, the one or more processors 202 may be configured to automatically turn off the plurality of lighting elements 208. In some embodiments, the fitness apparatus 200 may not include a light sensor 216.

Still referring to FIG. 2, the fitness apparatus 200 includes an accelerometer module 280. The accelerometer module 280 is communicatively coupled to the other components of the fitness apparatus 200 via the communication path 204. The accelerometer module 280 may be configured to determine fitness data such as calories burned, distance between the start position and the end position, average speed of the user while traversing from the start position to the end position, the speed travelled, and the like. In embodiments, fitness data may be computed using machine readable instructions stored in the one or more memory modules 206 and executed by the one or more processors 202.

Still referring to FIG. 2, the fitness apparatus 200 also includes a charging port 224. The charging port 224 is communicatively coupled to the one or more processors 202 and the power supply 212. In embodiments, the charging port 224 may be placed in the interior portion 106 of the shoe 100 (between the interior lining and shoe exterior of the top portion 102) or the tongue portion 110 of the shoe 100. In embodiments, the charging port 224 may be placed on an interior or exterior portion of apparel, such as a jacket 300 or pants, or gear, such as handbags 400B or backpacks 400A. In embodiments, the charging port 224 may be placed on an interior or exterior portion of apparel, such as a jacket or pants, or gear, such as handbags or backpacks. In embodiments, the charging port 224 may be a USB charging port.

Figure 3:
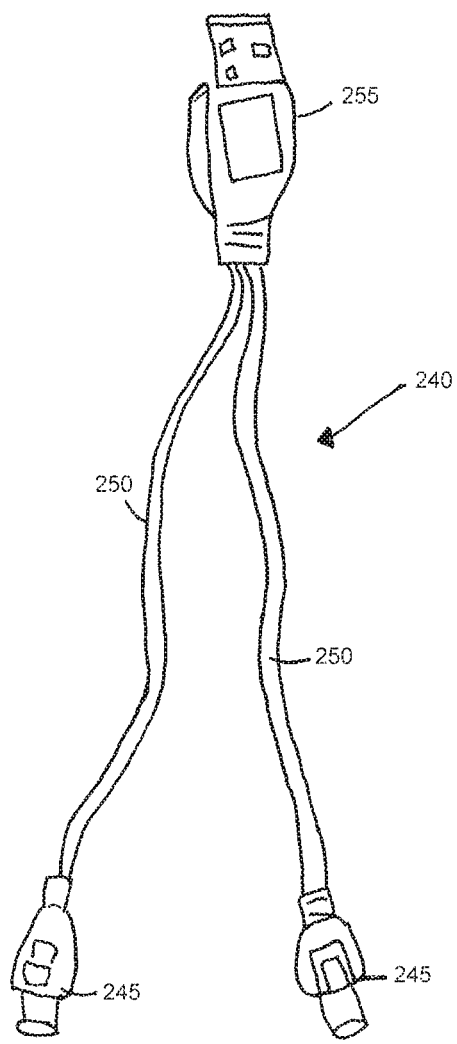
FIG. 3 illustrates a USB connector to charge the fitness apparatus, according to one or more embodiments shown and described herein.

Referring to FIG. 3, a USB connector 240 is shown. The USB connector 240 has two connecting wires 250. The two connecting wires 250 may be USB connecting wires 250 which join at one USB connecting plug 255. At each end of the USB connecting wires, a pin 245 is placed. Each pin 245 may be a USB pin which is configured to engage with the charging port 224. In embodiments, two USB connecting wires 250 and two USB pins 245 are provided so that a left shoe 100 and a right shoe 100 may be charged using one USB connector 240.

Figure 4:
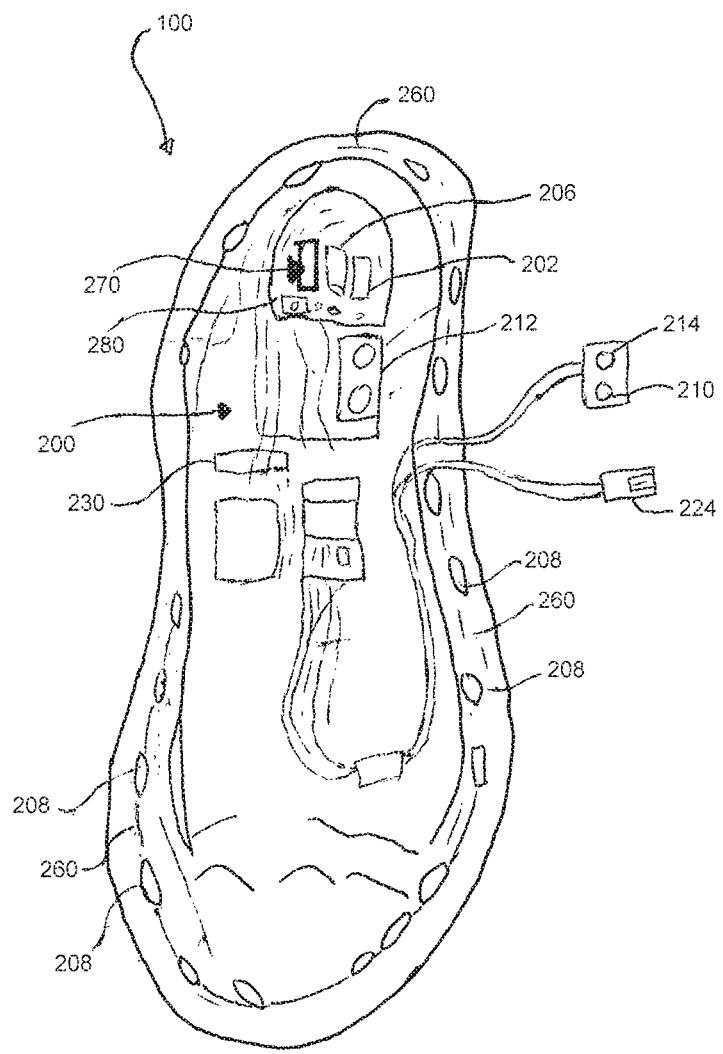
FIG. 4 illustrates the fitness apparatus and its various components fitted to the shoe, according to one or more embodiments shown and described herein.

Referring to FIG. 4, the sole portion 104 of the shoe 100 (shown here without the top portion 102) fitted with the fitness apparatus 200 is shown. The sole portion 104 is configured to accommodate the plurality of lighting elements 208, the lighting power switch 210, the GPS power switch 214, the power supply 212 and the satellite antenna 230 in addition to the other components (not shown). The plurality of lighting elements 208 are disposed around the sole portion 104 of the shoe 100. Each of the plurality of lighting elements 208 are connected to other of the plurality of lighting elements 208 with wiring 260. In embodiments, the plurality of lighting elements 208 may be powered on or off using the lighting power switch 210. In embodiments, the plurality of lighting elements 208 are connected via the wiring 260 to a PCB (printed-circuit-board) chip 270. In embodiments, the PCB chip 270 includes the one or more processors 202 and the one or more memory modules 206, the power supply 212, and the satellite antenna 230 in addition to the other components (not shown) depicted in FIG. 2. In embodiments, the PCB chip 270 is configured with machine readable instructions stored in the one or more memory modules 206 that cause the fitness apparatus 200 to perform various fitness determination tasks when executed by the one or more processors 202.

Still referring to FIG. 4, the power supply 212 includes the GPS chip. Further, the GPS chip is communicatively coupled to the satellite antenna 230. The satellite antenna 230 is configured to send and receive GPS location information regarding the start position, the stop position, the current position, and the like. Further, the GPS power switch 214 may be used to power on and off the GPS chip of the power supply 212. In some embodiments, the sole portion 104 of the shoe 100 may also have the charging port 224.

In some embodiments, the PCB chip 270 may also be configured to include an accelerometer module 280. The accelerometer module 280 may be configured to determine fitness data such as calories burned, distance between the start position and the end position, average speed of the user while traversing from the start position to the end position, the speed travelled, and the like. In embodiments, the accelerometer module 280 may also be configured to determine cadence or revolutions per minute, when the fitness apparatus is being used for cycling activities. Further, the accelerometer module 280 may be configured to determine an acceleration rate or speed rate during the route traveled. Additionally, the accelerometer module 280 may also be configured to measure the number of steps taken, activity intensity, speed of movement such as running or cycling, and metrics related to average and maximum speed or acceleration between the start position and the end position.

In embodiments, the fitness data may be transmitted to the display device 228 via the RFID chip, the Bluetooth® chip, WiFi chip, or a combination thereof, supporting wireless and GSM network data communications such as general packet radio system (GPRS). The accelerometer module 280 in the shoe will give more accurate data readings than in watches because they measure actual cadence of the foot.

Figure 5:
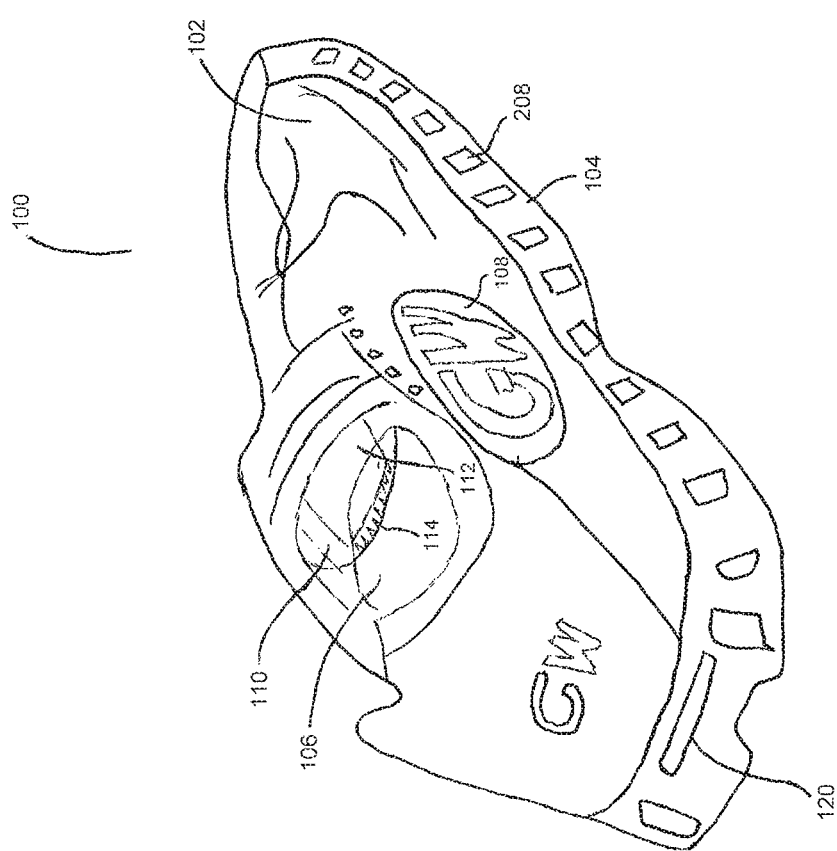
FIG. 5 illustrates the various locations a PCB chip may be disposed at the shoe, according to one or more embodiments shown and described herein.

FIG. 5 depicts an alternative location for placing the fitness apparatus 200 within the shoe 100. The PCB chip 270 may be placed within a slot 120. The slot 120 is disposed at the sole portion 104 of the shoe 100. In embodiments, the slot 120 may be disposed above the sole portion 104 at the top portion 102 of the shoe 100. In some embodiments, the PCB chip 270 may be disposed within a pouch 112 built within the tongue portion 110 of the shoe 100. The pouch 112 may be accessed with tongue attachment members 114. In embodiments, tongue attachment members 114 include hooks and loops, press buttons, zippers, Velcro™ or the like, which may be used to open or close the pouch 112.

Referring to FIG. 5, the PCB chip 270 may be disposed within and removed from the slot 120 or the pouch 112. In such embodiments, the power supply 212 is also disposed within the slot 120 or the pouch 112. Further, the lighting power switch 210, and the GPS power switch 214 are disposed at the interior portion 106 of the shoe. In embodiments, the PCB chip 270 may be removed and connected into a USB port on a laptop or computer to retrieve fitness data such as the distance traveled between the start position and the end position, the calories burned, the current position, the speed traveled, and the like. In embodiments, the PCB chip 270 when connected to a laptop or computer may also be used to re-set fitness data on the PCB chip 270.

Figure 6:
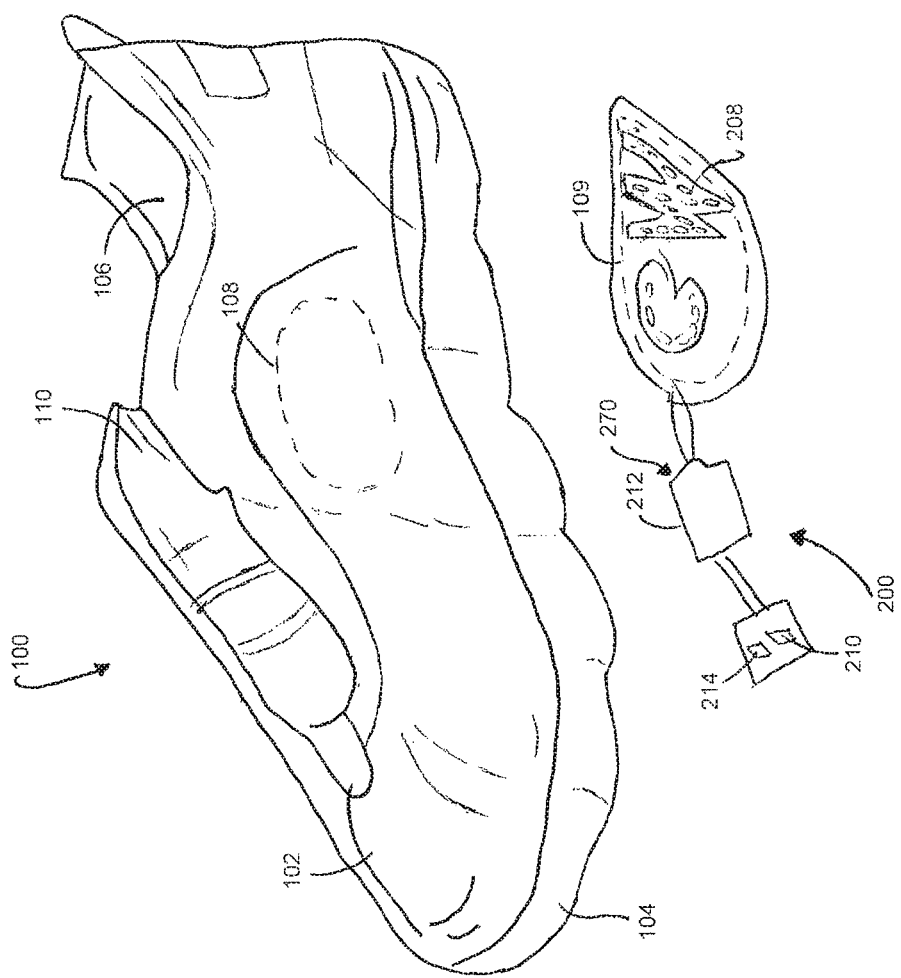
FIG. 6 illustrates the placement of a logo on a logo portion of the shoe, according to one or more embodiments shown and described herein.

FIG. 6 depicts placement of a logo 109 on the shoe 100. The logo 109 may be made of fabric or synthetic material, and carries the brand of the shoe 100. The logo 109 may be placed on light guide film (LGF) containing LEDs. In some embodiments, the light guide film (LGF) may be coupled to the PCB chip 270. In embodiments, the light guide film may be coupled to the lighting power switch 210 and the power supply 212. In other embodiments, the light guide film may be coupled to a separate light guide film power switch and a light guide film power supply, such that the light guide film operates independently of the plurality of lighting elements 208. Further, in some embodiments, the light guide film is rechargeable and may be charged by the charging ports 224. In other embodiments, the light guide film may be coupled a second PCB chip 270. In embodiments, the logo 109 may have the plurality of lighting elements 208 disposed in or around the logo 109. In some embodiments, the plurality of lighting 208 may be disposed such that the logo 109 spells a name of the brand. In embodiments, the logo 109 is disposed at the logo portion 108 of the shoe 100. In some embodiments, the logo 109 may also be disposed at a front portion or a back portion of the shoe 100. In embodiments, the plurality of lighting elements 208 disposed at the logo 109 may be communicatively coupled to the PCB chip 270. In some embodiments, the plurality of lighting elements 208 may be communicatively coupled to the power supply 212. In embodiments, the PCB chip 270 may be disposed within the pouch 112 of the tongue portion 110 of the shoe 100. Further, the plurality of lighting elements 208 disposed at the logo 109 may be communicatively coupled to the lighting power switch 210 configured to power on and off the plurality of lighting elements 208.

Figure 7:
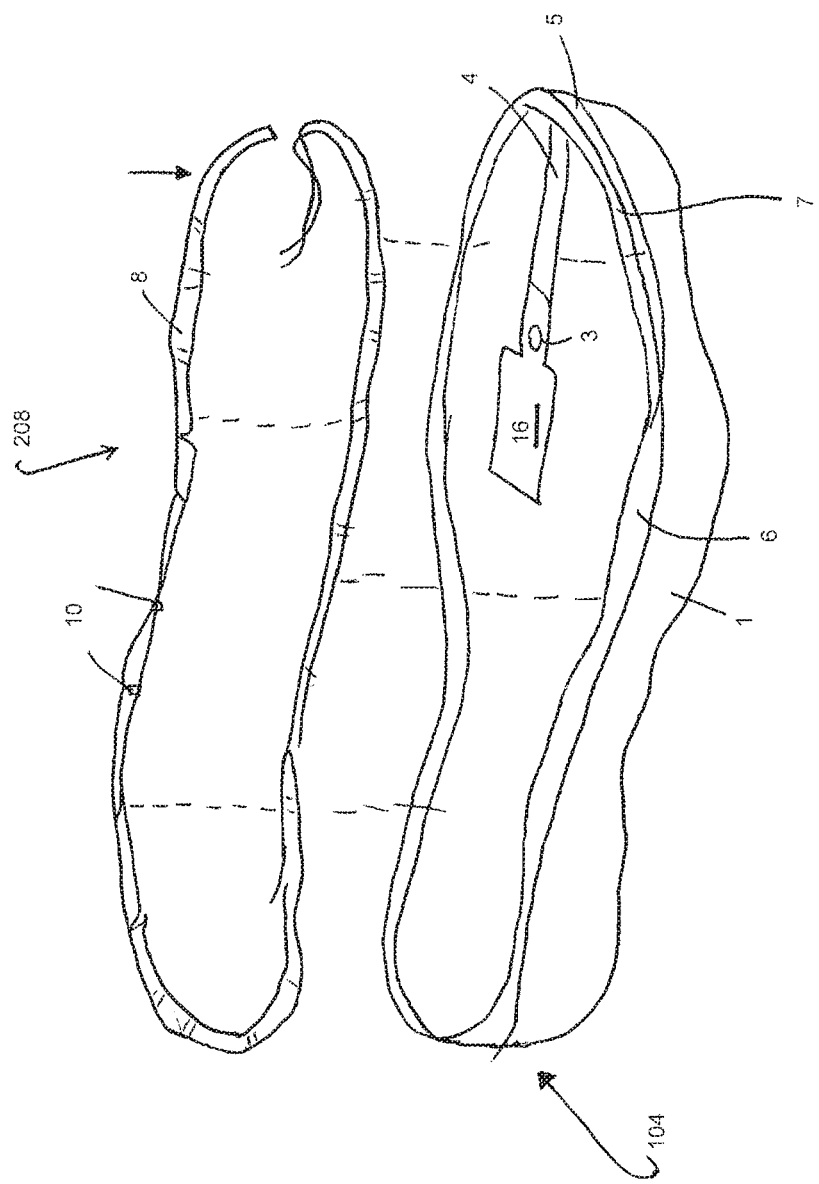
FIG. 7 illustrates the sole portion of the shoe including the outsole and a plurality of lighting elements, according to one or more embodiments shown and described herein.
Figure 8:
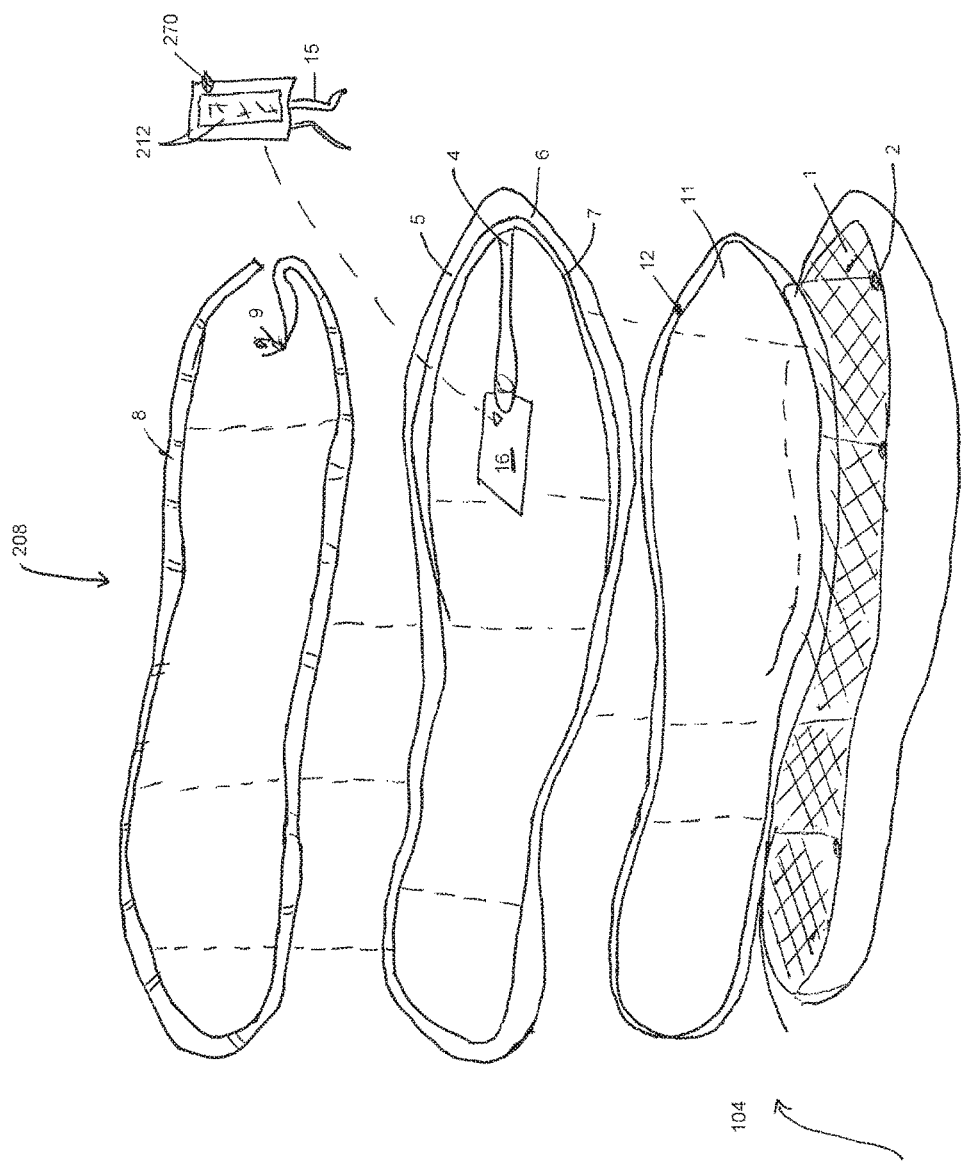
FIG. 8 illustrates the sole portion of the shoe including the outsole, the midsole, the air cushion and the plurality of lighting elements, according to one or more embodiments shown and described herein.

Referring to FIGS. 7 and 8 collectively, placement of the plurality of lighting elements 208 disposed at the sole portion 104 of the shoe 100 is shown. The sole portion 104 includes an outsole 1, a raised block 2, a through-hole 3, a straight-slot 4, a midsole 5, an air cushion groove 6, a lighting groove 7, a flexible lighting strip 8, an electrical plug 9, a lighting bead 10, an air cushion 11, a notch 12, the power supply 212, the PCB chip 270, a wire 15 and a recess 16.

In embodiments, the sole portion includes the outsole 1, the midsole 5 and the air cushion 11. In embodiments, the back portion of the outsole 1 makes contact with a ground. Further, the front portion of the outsole 1, the air cushion 11 and the midsole 5 are fitted into each other, as shown. The air cushion groove 6 is formed along an edge of the midsole 5. In a back-portion of the midsole 5, the lighting groove 7 is formed by offsetting a profile of the air cushion groove 6. The flexible lighting strips 8 including lighting beads 10 (together making the plurality of lighting elements 208) are placed within the lighting groove 7. In embodiments, end terminals of the flexible lighting strips 8 may be connected to the electrical plug 9.

In embodiments, at the back-side of the midsole 5, the lighting groove 7 is merged into the straight-slot 4. In embodiments, at the end of the straight-slot 4 an aperture/through-hole 3 may be disposed. The recess 16 is formed in the front-side of the midsole 5. In embodiments, the air cushion 11, which may be transparent, is fitted into the air cushion groove 6, such that the midsole 5 and air cushion 11 clamp the flexible lighting strip 8. Further, in embodiments, the PCB chip 270 (and the power supply 212) may be placed in the recess 16. In embodiments, the power supply 212 may include chargeable lithium battery. The shoe's 100 interior portion 106 may also include a charging port 224 for the chargeable lithium battery, and the lighting power switch 210.

Figure 9:
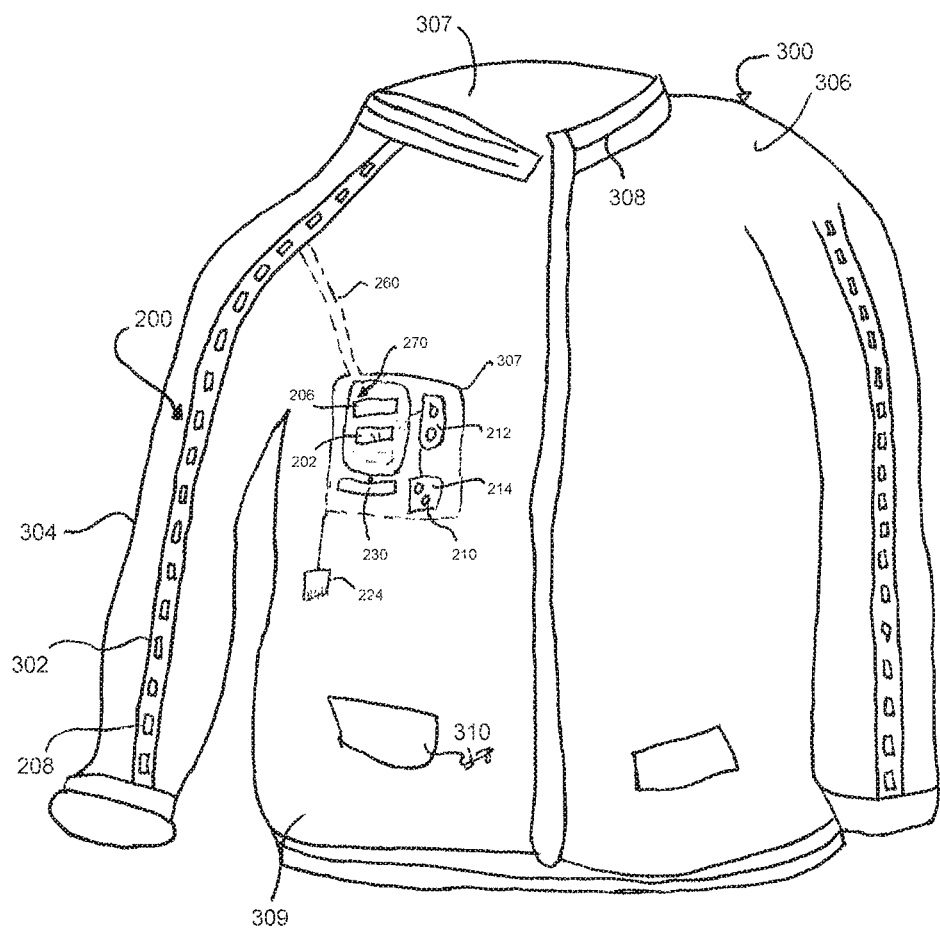
FIG. 9 illustrates the fitness apparatus and its various components fitted to apparel such as a jacket, according to one or more embodiments shown and described herein.
Figure 10:
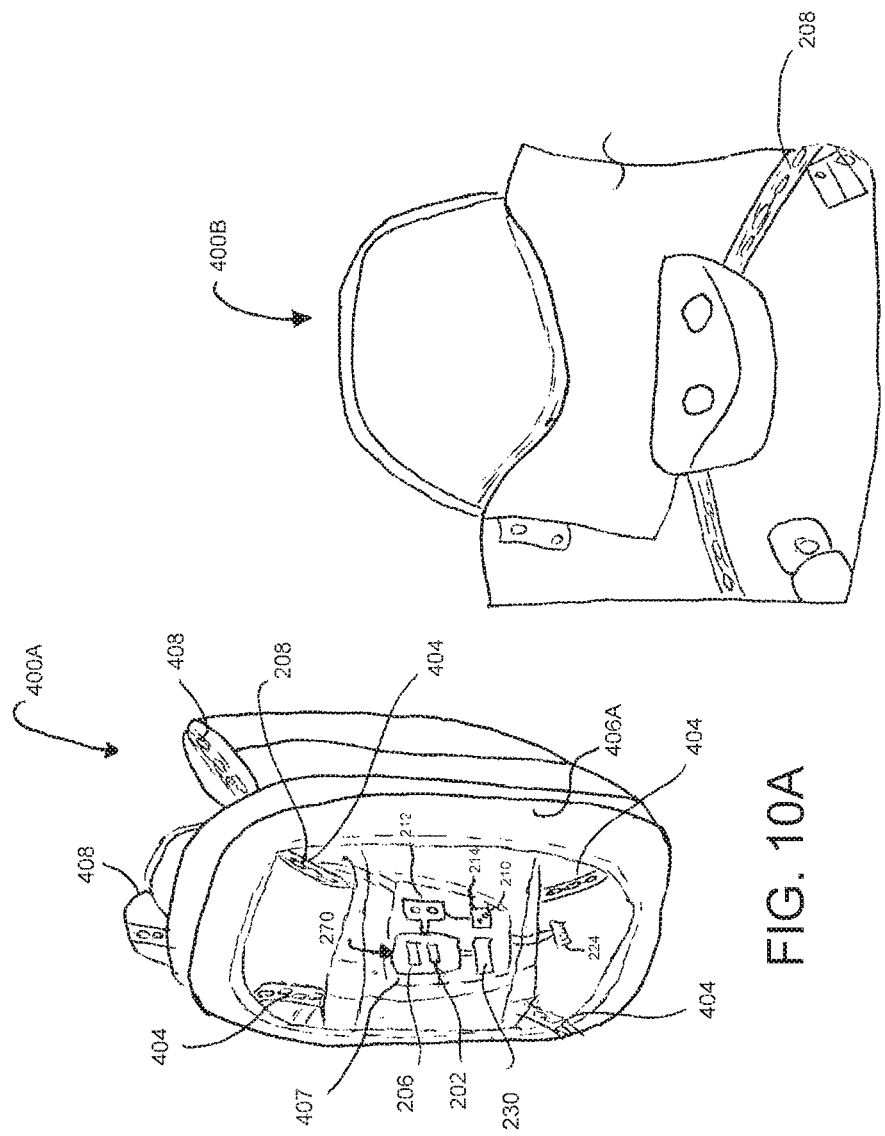
FIGS. 10A and 10B illustrate the fitness apparatus and its various components fitted to gear, such as a backpack (FIG. 10A) and a handbag (FIG. 10B), according to one or more embodiments shown and described herein.

Referring to FIG. 9, the fitness apparatus 200 is fitted to apparel or a clothing item such as a jacket 300. The plurality of lighting elements 208 are placed on an exterior portion 306 of the jacket 300. As shown, the plurality of lighting elements 208 are placed on sleeves 304 of the jacket 300. The plurality of lighting elements 208 are attached to the sleeves 304 with attachment members 302. In embodiments, attachment members 302 include hooks and loops, zippers, Velcro™ and the like. In some embodiments, the plurality of lighting elements 208 may be detachably attachable to the jacket 300. In embodiments, the plurality of lighting elements 208 may be also placed at a collar portion 308 or around a pocket region 310 of the jacket 300. Further, the plurality of lighting elements may be placed on trim lines, or stitched lines of the jacket 300.

In embodiments, the jacket 300 further includes an interior portion 307. As shown, the PCB chip 270 may be placed at the interior portion 307 of the jacket 300. In some embodiments, the PCB chip 270 may be placed at the interior portion 307 in a compartment or zipped pocket. In embodiments the PCB chip 270 may be attached to the interior portion 307 using attachment members 302. As described with reference to FIG. 4, the PCB chip 270 includes one or more processors 202 and one or more memory modules 206 which are communicatively coupled to the power supply 212 including the GPS chip, the satellite antenna 230, the lighting power switch 210, the GPS power switch 214. The charging port 224 is shown placed at the interior portion 307 of the jacket 300. While the PCB chip 270, the power supply 212 including the GPS chip, the satellite antenna 230, the lighting power switch 210, the GPS power switch 214 and the charging port 224 are shown placed on the interior portion 307, in some embodiments, these components may be alternatively placed on an exterior portion of the jacket 300.

In some embodiments, the fitness apparatus 200 may be placed on other apparel or clothing items such as a shirt, a t-shirt, a pair of pants, a pair of shorts, a skirt or a dress. In embodiments, apparel may also include athletic apparel such as a track warm up suit, or a cycling jersey. Further, the clothing item may also include a logo 109 (as discussed with respect to the shoe 100). The logo 109 may be made of fabric or synthetic material, and carries the brand of the apparel, such as the jacket 300. The logo 109 may be placed on light guide film (LGF). In some embodiments, the light guide film (LGF) may be coupled to the PCB chip 270. In embodiments, the light guide film may be coupled to the lighting power switch 210 and the power supply 212. In other embodiments, the light guide film may be coupled to a separate light guide film power switch and a light guide film power supply, such that the light guide film operates independently of the plurality of lighting elements 208. Further, in some embodiments, the light guide film is rechargeable and may be charged by the charging ports 224. In other embodiments, the light guide film may be coupled a second PCB chip 270.

Referring now to FIGS. 10A and 10B, the fitness apparatus 200 the fitness apparatus 200 is fitted to gear such as a backpack 400A or a handbag 400B. The plurality of lighting elements 208 are placed on an exterior portion 406 of the backpack 400A, as shown. As shown, the plurality of lighting elements 208 are placed on trims 404 of the backpack 400A. The plurality of lighting elements 208 are attached to the sleeves 304 with attachment members. In embodiments, attachment members include hooks and loops, zippers, Velcro™ and the like. In some embodiments, the plurality of lighting elements 208 may be detachably attachable to the backpack 400A. In embodiments, the plurality of lighting elements 208 may be also placed on straps 408 of the backpack 400A.

In embodiments, the backpack 400A further includes an interior portion 407. As shown, the PCB chip 270 may be placed at the interior portion 407 of the backpack 400A. In embodiments the PCB chip 270 may be attached to the interior portion 407 using attachment members. As described with reference to FIGS. 4 and 5, the PCB chip 270 includes one or more processors 202 and one or more memory modules 206, the power supply 212 including the GPS chip, and the satellite antenna 230 placed at the interior portion 407 of the backpack along with the lighting power switch 210 and the GPS power switch 214, and the charging port 224. The charging port 224 is shown placed at the interior portion 307 of the jacket 300. While the PCB chip 270, the lighting power switch 210, the GPS power switch 214 and the charging port 224 are shown placed on the interior portion 307, in some embodiments, these components may be alternatively placed on an exterior portion of the backpack 400A.

EXAMPLES

Example 1

Fitness Apparatus with a Shoe

In embodiments, when the fitness apparatus is fitted in shoes, the shoes may utilize a glowing logo using light thin-film guide technology (LFG) which utilizes electroluminenescence (EL) wire in which a light film plate emits light in response to the passage of an electrical current. The EL film produces single-frequency (monochromatic) light that has very narrow bandwidth, is absolutely uniform and visible from a great distance.

In embodiments, the battery (power source) is put in pouch/slot under the tongue of the shoe. The thin-plate is connected to printed-circuit board (PCB) that contains the electronic circuit and components such as transistors and logic gates that interface with the thin-film plate. The battery has a switch that can turn the logo on and off. In embodiments, there may be a switch that allows the user to change the color (red, orange, yellow, green, blue, violet, aqua and white) and/or mode of the light-film (e.g. fade, blink)

In embodiments, the shoes may include GPS chip, antennas, wireless transmitter, and software embedded in the chip module on the PCB to communicate and interface with a wireless receiver such as a smart phone. While the embodiment envisions that running or track shoes would be used, the embodiment is applicable to walking, hiking, and other types of shoes, even boots.

The shoes may have motion sensors, light sensors, gyroscope, and accelerometers that can measure (average) speed, distance, and estimated calories burned for a given "trip" that the user can set and reset back to 0 and automatically turn on the LED lights in the bottoms. In embodiments, the accelerometer chip could include: (i) three-axis magnetic field accelerometer module; (ii) compact size 0.4" inches wide×0.5" inches long×0.15" thick; (iii) low weight (e.g. 3 g); (iv) low power supply; (iv) sensor chip: ADXL335; (v) operating voltage range: 3v~5v; (vi) low supply and current consumption: 400 ua; (vii) interface: analog quantity output; (viii) operating temperature: −40'c~ to +85'c; (ix) built-in 5v tolerance protection; (x) selectable sensitivity (1.5 g/6 g); (xi) sleep mode: 3 μa; (xii) low voltage operation: 2.2 v-3.6 v; and (xiii) high sensitivity (800 mv/g @ 1.5 g).

In some embodiments, accelerometer chip can be inserted in a slot in the base of the heel of the shoe, in a compartment on the bottom of the shoe (or beneath the sole) that can be opened and closed or placed in a slot compartment that zips into the tongue of the shoe. This ensures that the accelerometer chip can be secured in the shoe while allowing the user to access it and remove it. The user can plug a USB stick to get the data from the module.

In some embodiments, the accelerometer chip will also contain an interface with a wireless transmitter to send computed data from trips to wireless receiver such as devices like smart phones and smart watches so the user can track distance traveled, average speed, and calories burned.

In embodiments, the shoes may utilize light sensors on the soles. The light sensors can be used to automatically activate (turn on) the LED lights as it becomes dark outside, so that the user does not have to stop to turn them on while running. The shoes may include an (analog) light sensor(s) (also known as photocells, light-dependent resistors, or photoresistors) so that the sole LEDs may automatically be turned on when the light outside become dim or dark, e.g. dusk or night. The sensors filter the amount of ambient light coming though a small lens and cause the switch of the circuit in the LED strip to be activated. In some embodiments, a pull-up resistor whose value is modified according to the amount of ambient light detected. The amount of light detected is converted from a digital signal to an analog input voltage signal. Likewise, the output voltage that goes into the analog input pin of the driver or microcontroller unit uses an appropriate analog-to-digital (A/D) converter. The light sensor could be implemented in the back heel of the shoe or along the midsole. The sensor is connected to the circuit containing the switch of the shoe by wires. When the resistor value exceeds a certain threshold, it will activate the switch by sending an output of a certain voltage to the power and driver unit that will turn the LEDs on. Many analog sensors come with 3 connection pins, one for receiving (input) voltage (Vcc), one for ground connection (GND), and one for output voltage pin (OUT). Modifications of the embodiments enable the user to turn LEDs on/off, control and change colors and modes (strobe, flashing) of LEDs remotely from a smart watch or smart phone so that users do not have to manually change by pressing the switch on the inside of the shoe.

In embodiments, degradation of static non-RCB colors of LED lights may occur. To prevent degradation of static non-RGB LED colors (which are composed of different combinations of RGB colors (e.g. purple or yellow) whereby these RGB colors will start appearing in parts of the diffuse lighting of the non-RGB color), aluminum may be used as conducting material in the wires and LED strip since aluminum has one of the highest conductivity of any metal.

In embodiments, the fitness apparatus uses LED power and a driver unit to control the LED lights, to enable control of the lighting power switch which may be controlled manually. Further, the power supply of the flexible LED strip is connected to a chargeable lithium battery, so that the fitness apparatus may be charged and used continuously. When the shoes are recharging, a red indicator light in the driver unit lights up the bottom of the outsoles. This indicator light turns green and the bottom of the outsoles light up green when the lithium battery is fully charged so that the user can remove the USB charging cables from the charging ports in the shoes.

In some embodiments, ribbon cables merge various wires connecting the LED lights together. The ribbon cables may be connected or disconnected based on usage to conserve battery. In embodiments, this may be accomplished by removing the tongue of the insole and opening the recess compartment in the midsole that contains power supply and driver unit.

In some embodiments, LED grooves built within the sole portion of the shoe may be used to fit/insert/accommodate the flexible LED strip containing LED light beads, which can reliably be secured in the LED groove. Some embodiments also use an air cushion to protect the LED strip and enhance the light transmission. Meanwhile, the air cushion can improve soles' elasticity and LED's lighting transmission effectiveness including uniform light distribution around the soles. In addition, the outsoles can be made of materials such as a semi-clear synthetic rubber that can also improve the uniform distribution of the light so that the light emitted from the LEDs does not appear brighter (e.g. concentrated) only around the LED beads.

In embodiments, the illuminated logo utilizes a separate re-chargeable lithium battery connected to the light-film guide (LFG). In embodiments, the rechargeable battery may be inserted into a zipped pouch beneath the tongue of the shoe. Accent lines on the shoe may be illuminated by connecting and feeding wires from electroluminescence (EL) strips or LFG strips inside the lining between the outside and interior portion of the upper shoe body to the wires in the recess compartment connected to the power or to its own separate power source/battery that can be inserted in a compartment in the back of the shoe or under the tongue of the shoe.

In embodiments, motion sensors may also be used to interface with the accelerometer chip to provide more accurate (higher precision) speed and acceleration measurements. The embodiments enable the user to reset the data for a new trip so that metrics can be separately tracked for a given trip or accumulated/aggregated across trips. Some embodiments enable the battery/power supplies to the GPS and/or accelerometer chips to be recharged via USB.

In some embodiments, the GPS chip such as SIM28ML is a stand-alone or A-GPS receiver. With built-in LNA, the chip may relax an antenna requirement or external LNA. The GPS chip can track as low as −165 dBm signal without network assistance. It may have features such as: (i) GPSreceiver supports QZSS, SBAS ranging supports WAAS/EGNOS/MSAS/GAGAN; (ii) 22 tracking/66 acquisition channel, up to 210 prn channels; (iii) small size and footprint: e.g. 10.1×9.7×2.5 mm, 18-pin lcc package; (iv) 12 multi-tone active interference cancellers and jamming elimination; (v) indoor and outdoor multi-path detection and compensation; (vi) max nmea update rate up to 5 hz; (vi) operating temperature: −40 to +85° C.; (vii) interface: uart/uart1; (viii) accuracy: 2.5 m cep; (ix) rohs complaint; (x) pulse-per second (pps) gps time reference; (xi) adjustable duty cycle; (xii) typical accuracy: +/−10 ns; (xiii) advanced software features; (xiv) epo orbit prediction; (xv) advanced location awareness technology; (xvi) supports logger function; (xvii) supports interference cancellation (AIC).

In embodiments, the GPS chip provides complete signal processing from antenna input to host port in either NMEA messages. The GPS chip requires 2.8V to 4.3V power supply. The host port is configurable to UART. Host data and I/O signal levels are 2.85V CMOS compatible. The functional parts are GPS chip, SAW filter, LNA, antenna interface; communication interface; and control signals.

In embodiments, the fitness apparatus may utilize different GPS chips. In one non-limiting example, the power saving consumption (which is especially important when a user such a child is wearing the shoes) contain the chip as the GPS needs to transmit its location to their parent as long as possible, until the shoes are recharged. When the power is first applied, the GPS chip goes into operation mode.

In the embodiment, the power supply to the GPS chip is independent of the power source to the LED strips in the soles or the power to glowing logo. The GPS supports operating modes for reduced average power consumption like standby mode, backup mode, periodic mode, and location mode. For instance, in sleep mode, the receiver stays at full on power state. The GPS will wake up when the host sends the command through the communication interface. In backup mode, the GPS chip must be supplied by the V_BACKUP pin and the VCC power should be cut off. This module may not be able to achieve this mode through PMTK commands. In periodic mode, the GPS chip enters tracking or sleep mode according to the interval configured. Lastly, in location mode enables the GPS chip to adaptively adjust the on/off time to achieve balance of positioning accuracy and power consumption.

Some embodiments enable GPS chips with power consumption/conservation saving capabilities to be placed either in a zipped slot pouch beneath the shoe tongue or in a secure slot in the back of the shoe. The GPS chip may have its own power source independent of the LED lights.

In some embodiments, the LEDs in the soles are recharged using USB ports in the (interior lines) of the shoes and a switch to change color modes.

In embodiments, the data from the GPS and accelerometer chips is transmitted to wireless devices like smart watches and smart phones so that calories burned, distance, acceleration, average speed, and other fitness metrics may be tracked. Without limitation, the software in the chip can be programmed to add or remove metrics.

In embodiments, users can also control the lights on the shoe remotely through an app that runs on their smart watch or smart phone that will allow them to change the lighting settings such as color and mode (static, blinking, flashing, etc) wirelessly via Wi-Fi or Bluetooth where the shoe receiver can pair and sync with the transmitter in the smart watch or phone. This overcomes the drawback of the user having to manually stop walking or running to turn the lights on/off and to change modes. In addition, the user can program the app and set a timer so that the lights will automatically turn on at a certain time each day and turn off if there is no movement for more than a given amount of time thereby preserving the battery life.

Example 2

Fitness Apparatus with Apparel

Figure 11:
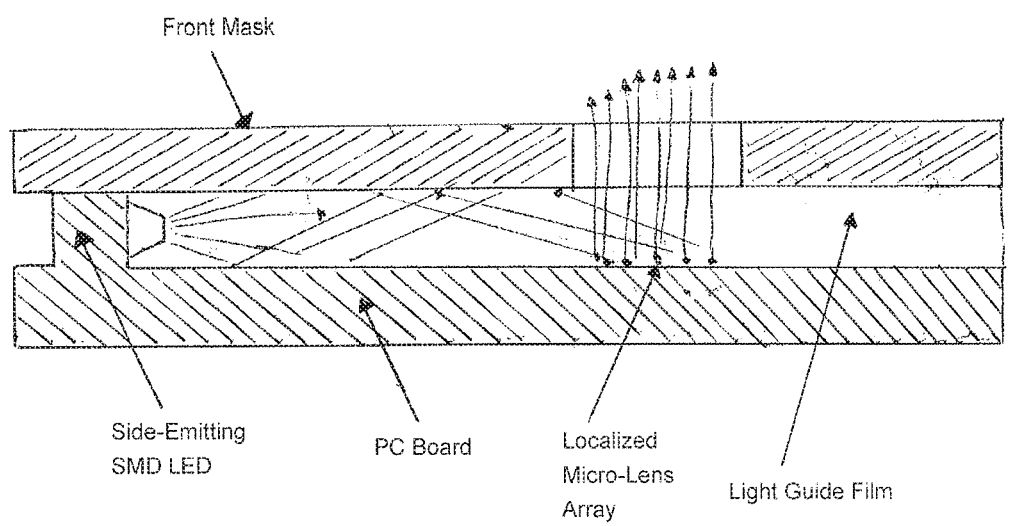
FIG. 11 illustrates light-film technology utilized to integrate LED or electroluminescence strips onto apparel or gear, according to one or more embodiments shown and described herein.

In embodiments, the LED/EL strips zip into place in the sports apparel like sleeves and pants of the track warm-up suits. Other embodiments utilize light-film technology to integrate light film into the fabric so that it lights up and illuminates. For instance, the logo can be illuminated in the apparel similar to the way it is illuminated and glows in the shoes. The light-film provides uniform lighting. Light from the LED sources is internally reflected down the length of the light film guide to various viewing areas. In some embodiments, as shown in FIG. 11, a front mask is used, which is the top layer, where the logo/image is placed using a UV adhesive on a polycarbonate or PMMA plastic. The middle layer contains the light guide film (LGF) which includes the localized micro-lens array. The localized micro-lends arrays redirect light out of the film to the viewer only where it is needed (e.g. to the logo/image). The LGF contains side-emitting SMD LEDs whose light is redirected by the localized micro-lens array. The localized micro-lens array enables a uniform and efficient distribution of light. The PCB contains semiconductors and embedded software to control the lighting (e.g. color). In embodiments, the LGF can be 0.075-0.4 mm in thickness.

In some embodiments, the LED lights of the fitness apparatus are typically 0.2 to 0.8 mm in height in proportion to the thickness of the LGF. The LGF is made of an optical grade polycarbonate. The LGF is connected to a print circuit board (PCB). In embodiments, the PCB board is waterproof. The PCB is connected to a battery such as a polycarbonate lithium ion battery. The battery contains a switch to turn the battery on/off. The embodiment utilizes LFG technology to light logos and other images on apparel. The apparel embodiments may also utilize carbon nanotubes to provide infrared heat to LFG to provide heat in the apparel, e.g. cycling jerseys, in cold temperatures.

In embodiments, the apparel may also utilize EL strips instead of LED strips down the sleeves as well as pants to make design patterns on the apparel. (An electro luminescent lights electrically similar to a capacitor—two conducting surfaces (light-emitting phosphor layer with a dielectric layer in between). EL lamps illuminate when powered with AC power. As voltage is applied to the conductive surfaces, an electric field is generated across the phosphor and dielectric layers. Twice during each cycle, electrons are excited and emit light through the transparent front electrode. The embodiments enable the power in the LED strips and EL strips in the apparel with a lithium ion battery to be recharged via USB. The LED strips, EL strips, and LFG for the glowing logo are all water proof.

The basic building block for the EL strip light is aluminum foil. Serving as the back electrode, the foil has dielectric coating applied to give the light strip high voltage integrity. A layer of light emitting phosphor is then applied. Screened onto the phosphor is the transparent front electrode, which defines the lit area. On top of the electrode an opaque bus bar is screened, to provide a more uniform electric field across the entire light surface, insuring more uniform luminance. Front and back leads, specially treated to insure the moisture barrier is not compromised, are applied to provide power access. Finally, the entire sandwich is enclosed in an Aclar package to protect the light from exposure to environment, especially moisture, and to provide electric insulation.

In embodiments, LED/EL strips are used to illuminate the sleeves and arms of (sports) apparel while utilizing LFG technology described herein to illuminate logos and images on apparel. The embodiments enable users to turn the strips on/off, change the colors in the strips, and to add or remove the strips by zipping/unzipping them from the sleeves and/or pants so the apparel can be worn with or without them or removed to wash the apparel. The embodiments enable not just the logo and soles to illuminate and glow, but other parts of the shoe to illuminate and glow, such as lines and accents on the shoe or specific parts of the shoe using light-film guide (LFGs), EL wire, and/or optic fiber that are integrated and stitched into the shoe. The illuminated colors can rotate, remain static, or dynamically change. There is no limitation in the shape or lines that can be illuminated as the LFG, EL wires, or fiber optics are flexible enough to turn, rotate, and bend. Likewise, the LFG, EL wires, and/or fiber optics are not limited to the type of patterns, designs, and accent lines that can be illuminated on the apparel.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A shoe comprising:
a top portion;
a sole portion attached to the top portion;
a lining located in an interior portion;
one or more processors;
one or more memory modules communicatively coupled to the one or more processors;
a plurality of lighting elements coupled to the one or more processors, wherein two or more of the plurality of lighting elements are attached to the sole portion;
a logo portion, detachably located on an exterior portion of the shoe, wherein the logo portion comprises one or more of the plurality of lighting elements;
a power supply providing power to the plurality of lighting elements;
a lighting power switch configured to control the plurality of lighting elements disposed on the shoe;
a network interface hardware for sending and receiving fitness data; and
machine readable instructions stored in the one or more memory modules that cause the shoe to perform at least one of the following when executed by the one or more processors:
determine a distance travelled between a start position and an end position;
determine calories burned during the distance travelled;
activate the plurality of lighting elements in a lighting mode with a signal from the lighting power switch in response to determining the distance travelled or determining the calories burned; and
send fitness data indicative of the distance travelled, the calories burned, or the lighting mode.

2. The shoe of claim 1, wherein the machine readable instructions stored in the one or more memory modules that cause the shoe to perform at least one of the following when executed by the one or more processors:
determine the start position and the end position;
determine a current position;
determine a route travelled between the start position and the end position;
determine a speed travelled; and
send fitness data indicative of the start position, the end position, the current position, the route travelled, and the speed travelled.

3. The shoe of claim 1, further comprising:
a satellite antenna communicatively coupled to the one or more processors; and
a display device communicatively coupled to the network interface hardware, wherein fitness data is received and displayed on the display device.

4. The shoe of claim 1, wherein the machine readable instructions stored in the one or more memory modules that cause the shoe to perform at least the following when executed by the one or more processors to:
activate the plurality of lighting elements to display a first pre-selected lighting mode in response to obtaining a pre-selected distance goal; or
activate the plurality of lighting elements to display a second pre-selected lighting mode in response to obtaining a pre-selected calories goal.

5. The shoe of claim 1, wherein the machine readable instructions stored in the one or more memory modules that cause the shoe to perform at the following when executed by the one or more processors to:
map the route travelled from the start position to the end position and display the map on the display device.

6. The shoe of claim 1, wherein the machine readable instructions stored in the one or more memory modules that cause the shoe to perform at least the following when executed by the one or more processors to:
activate the plurality of lighting elements to display a third pre-selected lighting mode in response to charging the shoe; and
activate the plurality of lighting elements to display a fourth pre-selected lighting mode in response to completion of the charging.

7. The shoe of claim 1, further comprising a global position system (GPS) module power switch that is configured to control a GPS chip independent of the lighting power switch.

8. The shoe of claim 1, wherein the lighting mode is strobe lighting, blinking lighting, static lighting fading lighting, or a combination thereof.

9. The shoe of claim 1, further comprising a light sensor, wherein the machine readable instructions stored in the one or more memory modules that cause the shoe to perform at least the following when executed by the one or more processors to:

activate the plurality of lighting elements to automatically turn on in response to a dark external environment based on a determination by the light sensor.

10. The shoe of claim 1, further comprising a printed-circuit-board (PCB) chip comprising the one or more processors, the one or more memory modules, the power supply, the satellite antenna and an accelerometer module, wherein the PCB chip is disposed at a slot or a pouch of the shoe.

11. The shoe of claim 1, further comprising a charging port disposed at a tongue portion of the shoe, and configured to receive a connecting wire with a pin connecting to a USB port.

12. The shoe of claim 1, wherein the plurality of lighting elements are rechargeable LED lights.

13. The shoe of claim 1, wherein the plurality of lighting elements are disposed at the sole portion and a logo portion of the shoe, the lighting power switch and a global position system (GPS) power switch are disposed at an interior portion of the shoe, and the power supply is disposed within a slot or a pouch of the shoe.

14. A shoe comprising:
a top portion;
a sole portion attached to the top portion;
a lining located in an interior portion;
one or more processors;
one or more memory modules communicatively coupled to the one or more processors;
a plurality of lighting elements coupled to the one or more processors, wherein two or more of the plurality of lighting elements are attached to the sole portion;
a logo portion, detachably located on an exterior portion of the shoe, wherein the logo portion comprises one or more of the plurality of lighting elements;
a power supply providing power to the plurality of lighting elements;
a lighting power switch configured to control the plurality of lighting elements disposed on the shoe;
a network interface hardware for sending and receiving fitness data; and
machine readable instructions stored in the one or more memory modules that cause the shoe to perform at least one of the following when executed by the one or more processors:
determine a current position;
determine whether the current position is within a pre-determined radius from a reference position;
activate the plurality of lighting elements in a lighting mode in response to a signal from the lighting power switch; and
send fitness data indicative of the current position or the lighting mode.

15. The shoe of claim 14, wherein the machine readable instructions stored in the one or more memory modules that cause the shoe to perform at least the following when executed by the one or more processors:
determine a start position and an end position;
determine a distance travelled between the start position and the end position;
determine and map a route travelled between the start position and the end position;
determine calories burned during the distance travelled;
determine a speed travelled; and
send fitness data indicative of the start position, the end position, the distance travelled, the route travelled, the calories burned, or the speed travelled.

16. The shoe of claim 14, wherein the machine readable instructions stored in the one or more memory modules that cause the shoe to perform at least one of the following when executed by the one or more processors to:
send, automatically a notification indicative of the current position in response to the fitness apparatus being outside of the pre-determined radius to a display device.

17. The shoe of claim 14, further comprising:
a network interface hardware communicatively coupled to the one or more processors; and
a display device communicatively coupled to the network interface hardware, wherein fitness data is received and displayed on the display device.

* * * * *